(12) United States Patent
Brock

(10) Patent No.: US 7,594,918 B2
(45) Date of Patent: Sep. 29, 2009

(54) IMPLANT PLACEMENT LOCATOR INSTRUMENT

(76) Inventor: David L. Brock, 3 Noble Ct., Long Valley, NJ (US) 07853

( * ) Notice: Subject to any disclaimer, the term of this patent is extended or adjusted under 35 U.S.C. 154(b) by 1058 days.

(21) Appl. No.: 10/833,853

(22) Filed: Apr. 28, 2004

(65) Prior Publication Data
US 2005/0245940 A1  Nov. 3, 2005

(51) Int. Cl.
*A61B 17/58* (2006.01)
(52) U.S. Cl. ........................................ 606/99
(58) Field of Classification Search ............... 606/79, 606/86, 167, 172, 181; 433/74–76, 165
See application file for complete search history.

(56) References Cited

U.S. PATENT DOCUMENTS

| | | | |
|---|---|---|---|
| 5,636,986 A | 6/1997 | Pezeshkian | |
| 5,842,859 A | 12/1998 | Palacci | |
| 5,876,204 A | 3/1999 | Day et al. | |
| 5,967,777 A | 10/1999 | Klein et al. | |
| 5,976,142 A * | 11/1999 | Chin | 606/73 |
| 6,916,322 B2 * | 7/2005 | Jesch | 606/80 |
| 2005/0096686 A1 * | 5/2005 | Allen | 606/181 |

\* cited by examiner

*Primary Examiner*—Anhtuan T. Nguyen
*Assistant Examiner*—Michael J Araj
(74) *Attorney, Agent, or Firm*—Kenneth P. Glynn, Esq.

(57) ABSTRACT

An implant placement locator instrument includes an elongated handle member that has a first end and a second end, at least one of the first end and the second end being an operative end. The operative end includes a base having a footprint of an implant post. The base has a hollow center, and the hollow center is adapted to hold a punch. There is a punch located on the instrument at the operative end and inside the hollow center of the base, the punch having a pointed tip for piercing bone. The punch may be one end of the handle, and has a first position relative to the base, being a retracted position wherein it is retracted within the hollow center, and has a second position relative to the base, being an extended, piercing position wherein it is at least partially extended out of the hollow center. There is a spring connected to the base and the punch so as to enhance movement of the punch from one of its first position and second position to the other of its first position and second position.

10 Claims, 4 Drawing Sheets

IMPLANT PLACEMENT LOCATOR INSTRUMENT

BACKGROUND OF THE INVENTION

1. Field of the Invention

The present invention relates to dental practices and particularly to an instrument that aids in the proper locations for implants such as posts. The present invention implant locator instrument also aids in fixing a chosen location and in creating a started hole for subsequent drilling. Thus, the present invention device enables a practitioner to find a good location for an implant, to mark the situs, and to start the hole with a single instrument.

2. Information Disclosure Statement

The following prior art is representative of the state of the art in the general field of dental drilling and implanting:

U.S. Pat. No. 5,967,777 describes a surgical template and method for drilling osteotomies (e.g., holes in a jawbone) and installing one or more dental implants using a surgical template assembly. The surgical template assembly is provided with one or more drill guides and one or more dental implant guides. The guides are positioned in the surgical template assembly by a computer-driven milling machine interfaced with a computer-generated image of a patient's jawbone and a computer generated simulation of at least one dental implant so that when the surgical template is placed in the patient's mouth the trajectory of the guides in the surgical template into the patient's jawbone corresponds to a trajectory of the computer-generated simulation of the dental implant into the computer-generated image of the patient's jawbone. Preferably, three fiducial markers, provide positional coordination between the CT scan data, the computer-generated simulation of the dental implant, and the computer-driven milling machine.

U.S. Pat. No. 5,876,204 describes a dental positioning guide that has two pins connected to a hub section. The pins may be rotated to a plurality of angular positions.

U.S. Pat. No. 5,842,859 describes a method and indicating device for determining a location of a hole to be used as an attachment point for fixture or fixture part on an area of the human body are disclosed. The indicating device comprises a bearing part which is adapted to be received in an existing hole and a protruding part interconnected with the bearing part and extending above the existing hole when the bearing part is inserted into the existing hole. At least one indication part is interconnected with the protruding part and has a free end extending away from the existing hole, where a location of the new hole to be used as an attachment point is established at a position substantially adjacent to an exterior surface of the free end of the indicating part.

U.S. Pat. No. 5,636,986 describes a drill guide system for use in the installation of dental implants. The guides are configured in the shape of teeth and have drill brushings passing through to guide and position the drill so that the resulting hole will receive an implant that is properly positioned and aligned. The guides are provided in different configurations depending on the number of adjacent implants to be installed and have a depending pin to position the guide in initial drilled hole. By being configured in the shape of teeth, the dental surgeon is able to position the guide prior to drilling and be able to observe how the resulting work will appear once the actual prosthetics are installed on the implants. The drill bushings not only guide the drill but provide additional patient security since the possibility of slippage or breakage of the drill bit during the drilling is substantially reduced.

Notwithstanding the prior art, the present invention is neither taught nor rendered obvious thereby.

SUMMARY OF THE INVENTION

The present invention relates to an implant placement locator instrument. The instrument, or device, includes an elongated handle member. The handle member has a first end and a second end, at least one of the first end and the second end being an operative end. The operative end includes a base having a footprint of an implant post. The base has a hollow center, and the hollow center is adopted to hold a punch. There is a punch located on the instrument at the operative end and inside the hollow center of the base, the punch having a pointed tip for piercing bone. The punch has a first position relative to the base, being a retracted position wherein it is retracted within the hollow center, and has a second position relative to the base, being an extended, piercing position wherein it is at least partially extended out of the hollow center. There is a spring connected to one of the operative end base and the punch so as to enhance movement of the punch from one of its first position and second position to the other of its first position and second position.

A user may position the device at a location desirable for an implant post over a bone area and then actuate the device to move the punch from its first position to its second position to mark and pierce a bone area for subsequent preparative work for implanting a post, so as to create both a locator mark and a starter piercing for the subsequent preparative work. Typically, the gums are cut open and folded or otherwise moved out of the way for piercing, drilling and post insertion. These skills are well known and need not be elaborated upon herein.

In some embodiments, the punch is fixedly connected to the operative end of the elongated handle, and the base is moveably connected to the operative end of the elongated handle. In these embodiments, the base is connected to the operative end of the elongated handle via the spring, and the spring biases the base downwardly to a rest position wherein the punch is in its first position.

In some present invention embodiments, the base is a hollow cylindrical base. In some embodiments, the elongated handle is a hollow handle and the operative end has a terminus that is the base, and wherein the instrument further includes a punch shaft located within the elongated handle which has an actuation end and a punch end, and the punch end has a terminus that is the punch. The punch shaft may be connected to the elongated handle via the spring, and the spring will bias the punch shaft upwardly to a rest position wherein the punch is in its first position.

In many preferred embodiments, the first end of the elongated handle is a top, and the second end of the elongated handle is the operative end, and the punch shaft actuation end extends out of the top of the elongated handle, for actuation by depression.

In some embodiments, the elongated handle is a straight line with a single central axis, while in other embodiments the elongated handle includes at least one bend and the punch shaft actuation end extends out of the elongated handle at the bend.

The present invention also includes alternative implant placement locator instruments. These include an elongated handle member, the handle member having a first end and a second end, each of the first end and the second end being an operative end, with each operative end including: a base having a footprint of an implant post, the base having a hollow center, the hollow center being adopted to hold a punch. The punch is located on the instrument at the operative end and inside the hollow center of the base. The punch has a pointed tip for piercing bone, and the punch has a first position relative to the base, being a retracted position wherein it is retracted within the hollow center, and has a second position relative to the base, being an extended, piercing position wherein it is at least partially extended out of the hollow center. There is a spring connected to one of the operative end base and the punch so as to enhance movement of the punch from its one of its first position and second position to the other of its first position and second position. The features described earlier may likewise be included in these additional embodiments.

A user may position the device at a location desirable for an implant post over a bone area and then actuate the instrument to move the punch from its first position to its second position to mark and pierce a bone area for subsequent preparative work for implanting a post, so as to create both a locator mark and a starter piercing for the subsequent preparative work.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1:
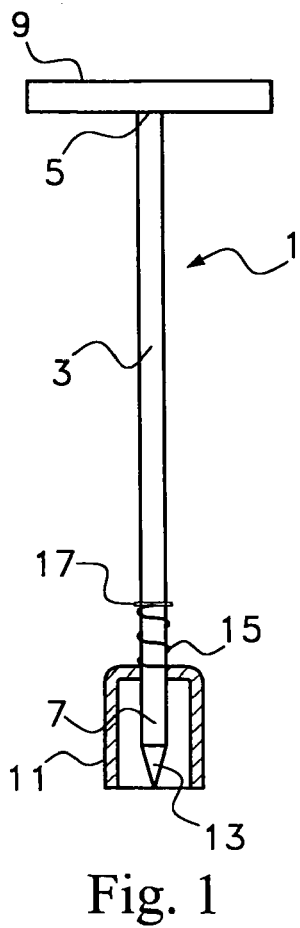
FIG. 1 illustrates a front, partially cut view of one embodiment of a present invention implant placement locator instrument.

FIG. 1 illustrates a front, partially cut view of a present invention implant placement locator instrument 1. It includes an elongated handle member 3, with a first end 5 and a second end 7, second end 7 being the operative end. There is a base 11, having a circular footprint (the footprint of a typical implant post), and having a hollow inside center as shown. Second end 7 terminates as a punch with a pointed tip 13. Flange 17 is rigidly attached to handle member 3 and the top end of spring 15 is fitted thereto. Flange 17 acts as a spring stop. The top of spring 17 may be forced fitted, welded or otherwise attached to either or both of flange 17 and handle member 3. The bottom of spring 17 is connected to base 11, and base 11 is slideable and moveable up and down second end 7, via spring compression and extension.

Figure 2:
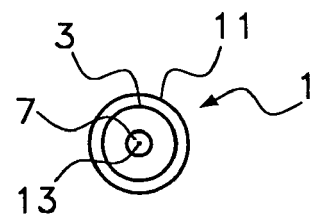
FIG. 2 shows a bottom view thereof.

FIG. 1 shows a first position for base 11, wherein it is in a rest position and punch tip 13 is retracted therein. FIG. 2 shows a bottom view thereof with identical parts identically numbered.

When base 11 is placed on a gum/bone post implant situs, it is first positioned and moved, if needed for repositioning, to locate a proper place for a post. Once front/back/left/right/spacing are properly selected, bar 9 may be pressed and tip 13 will protrude and move to a second position extended out of base 11.

Figure 3:
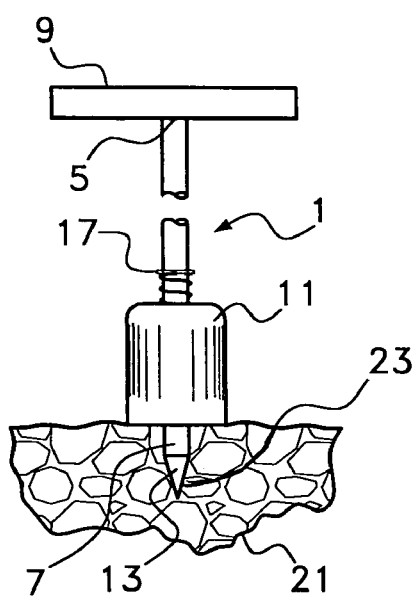
FIG. 3 shows a partial front view thereof with the pointed tip of the punch in the piercing mode.

FIG. 3 shows instrument 1 in use, with the same reference numerals as above. When bar 9 is pressed, tip 13 creates a starting hole 23 in bone 21, for subsequent drilling and post implant.

Figure 4:
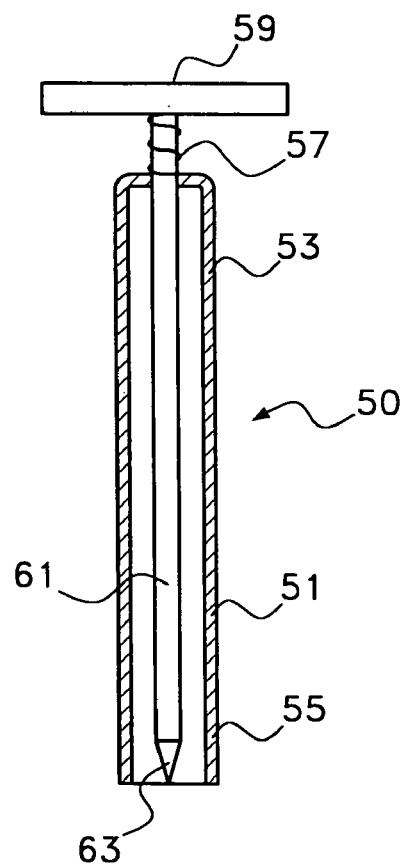
FIG. 4 shows a front, cut view of another present invention in a straight line, more encased version than is shown in the foregoing Figures.

FIG. 4 shows a front, cut view of another present invention in a straight line, more encased version than is shown in the foregoing Figures. Here, implant placement locator instrument 50 has a base 51 that extends nearly top to bottom. Base 51 has a top 53 and a bottom 55 and is hollow. Handle member 61 has a top bar and first end 59 and a pointed punch tip and second end 63. Spring 57 is connected to the top bar and first end 59 and to the top 53 of base 51, as shown. It is used in a fashion similar to present invention instrument 1 of FIGS. 1, 2 and 3 above.

Figure 5:
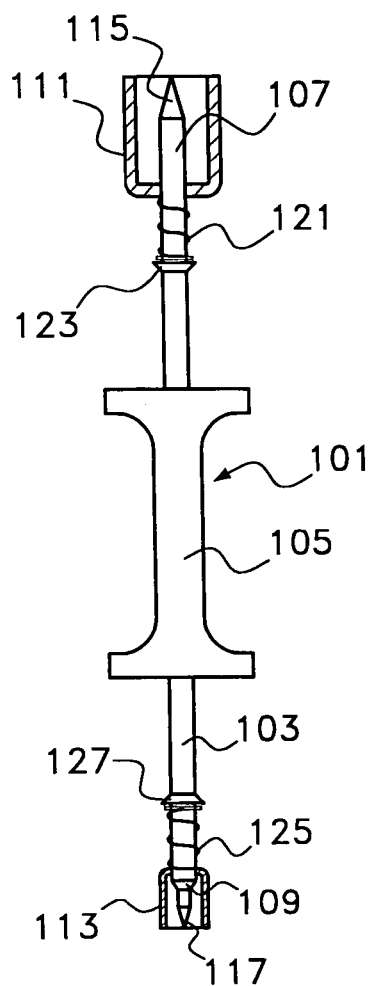
FIG. 5 shows a front, partially cut view of a present invention device that has two different size punches at opposite ends.

FIG. 5 shows a front, partially cut view of a present invention device 101 that has two different size bases/footprints at opposite ends. Device 101 has a handle member 103, with gripping area 105, operative first end 107 and operative second end 109. Each of these ends has punch tips, i.e., tips 115 and 117, respectively. Pointed tip 115 is larger in diameter than pointed tip 117, so that one may be used for a larger implant post than the other. At first end 107 is a base 111 connected to spring 121, that is held by stop flange 123. Likewise, at second end 109 is base 113, connected to spring 125, that is held by stop flange 127. This device can be used as either a large or small piercing device, wherein the user may select either end as the operative end.

Figure 6:
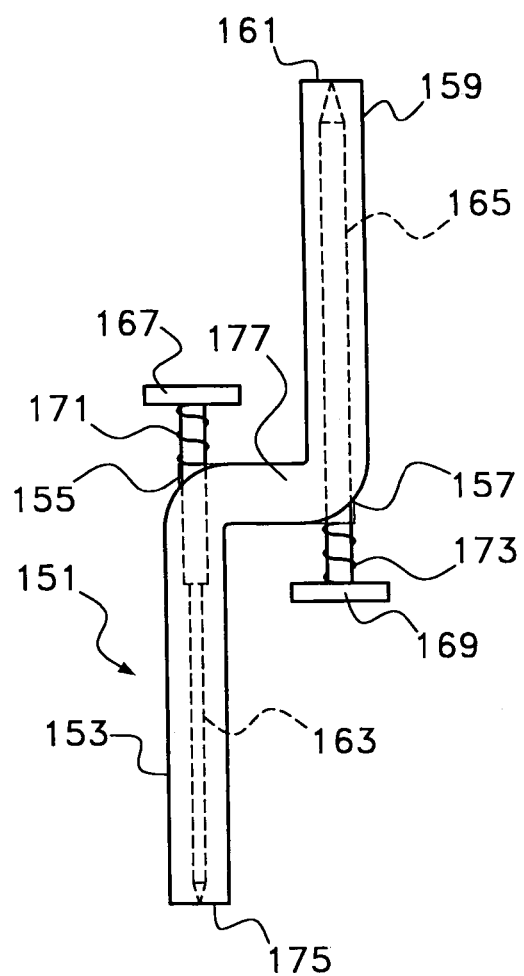
FIG. 6 illustrates another double punch embodiment of the present invention.

FIG. 6 illustrates another double punch embodiment of the present invention instrument 151. Instrument 151 has a first handle member 165 and a second handle member 163. Each handle member terminates at one end with a tip, and at the other with a bar 169 and 167, respectively. The base in this embodiment is an elongated housing for the two separate handle members, which are offset by two elbows. The base has a first gripping area 153, and operative first end 175, and a second gripping area 159, and operative second end 161. The two gripping areas have elbows 155 and 157 and are connected to the same central area 177. Each of the operative ends has a circular hollow area from which the pointed tip extends when pressed. The two handle members and their tips are maintained in a rest (retracted) position via springs 173 and 171, as shown. One pointed tip is larger in diameter than the other pointed tip.

Figure 7:
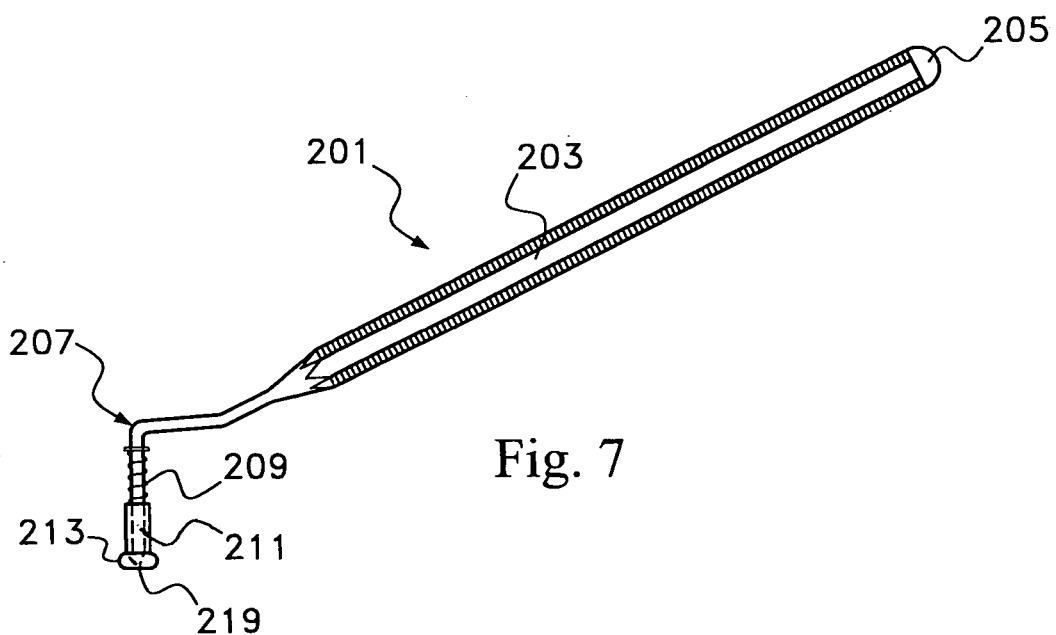
FIG. 7 and FIG. 8 show a side and a partially cut front view of a preferred embodiment of the present invention device.
Figure 8:
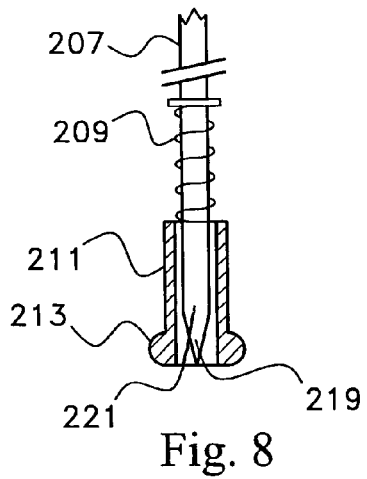

FIG. 7 and FIG. 8 show a side and a partially cut front view of a preferred embodiment present invention device 201. The preceding embodiments are presented to show concepts and variations and could be used as described. However, those would be impractical for areas toward the back of the mouth, due to the inability to assume a vertical posture relative to the bone with the devices having straight line designs. Hence, FIG. 7 and forward describe preferred embodiments of the present invention and represent some of the most practical and versatile embodiments.

Referring to both FIGS. 7 and 8, device 201 includes an elongated handle member 203, with a first end 205 and a second end 207, second end 207 being the operative end, and having bends therein to establish an appropriate angle (e.g., thirty degrees) with the opposite first end 205. This angle optimizes the use of the device 201 for otherwise difficult to reach work areas. There is a base 211, having a wider diameter foot 213, with a circular footprint (the footprint of a typical implant post), and having a hollow inside center, as shown. Second end 207 terminates as a punch 221 with a pointed tip 219. The top end of spring 209 is fitted to the handle and is restricted from movement up the handle by any means, including the bend being a stop, or otherwise as described above. For example, the top of spring 209 may be forced fitted, welded or otherwise attached to and handle member 203. The bottom of spring 209 is connected to base 211, and base 211 is slideable and moveable up and down second end 207, via spring compression and extension.

Figure 9:
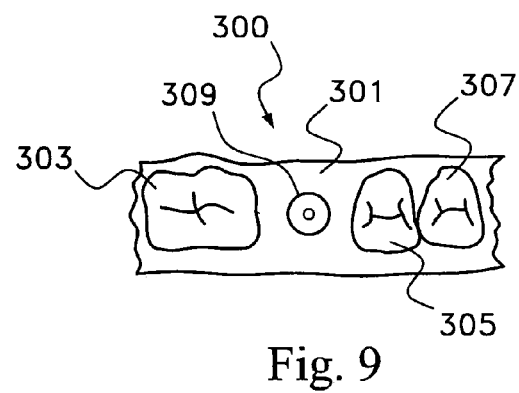
FIG. 9 shows a top view of a portion of a lower tooth, gum and bone area with a gap in need of a post.
Figure 10:
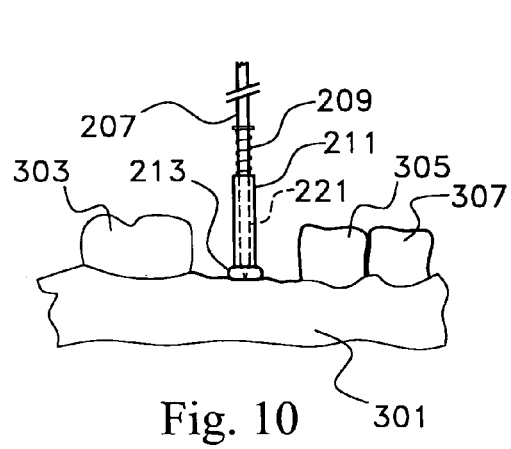
FIG. 10 shows the FIGS. 7/8 device in a partial front view in use with the aforesaid, for locating a proper post site; and, FIG. 11 shows the same view, but with the punch piercing tip penetrating the bone; and, FIG. 12 shows a front view of a preferred alternative embodiment present invention device with opposing, different size bases/footprints.
Figure 11:
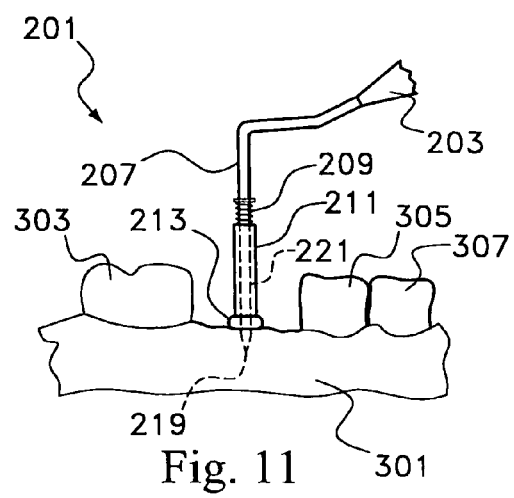

FIG. 9 shows a top view of a portion of a lower tooth, gum and bone area with a gap in need of a post and fitting. This represents a top view of a right lower rear tooth area. Tooth 303 is a molar, and teeth 305 and 307 are other teeth in gum/bone area 301. Footprint/punch hole 309 illustrates theoretically the desired area for locating a proper post site for a post. FIG. 10 shows the FIGS. 7/8 device in a partial front view in use with the aforesaid gum/bone area 301. (Partial gum removal and fold back is assumed and this is within the purview of the professional.) All parts previously numbered are numbered identically in this and the following FIG. 11. In FIG. 10, device 201 is positioned but not yet depressed. FIG. 11 shows the same view, but with the handle 203 pressed, and punch piercing tip 219 penetrating the bone area 301 (of position 309 shown in FIG. 9). When base 211 is placed on a gum/bone post implant situs, it is first positioned and moved, if needed for repositioning, to locate a proper place for a post. Once front/back/left/right/spacing are properly selected, handle 203 may be pressed and tip 219 will protrude and move to a second position extended out of base 211 to mark the desired location and create a pierced hole for subsequent drilling.

Figure 12:
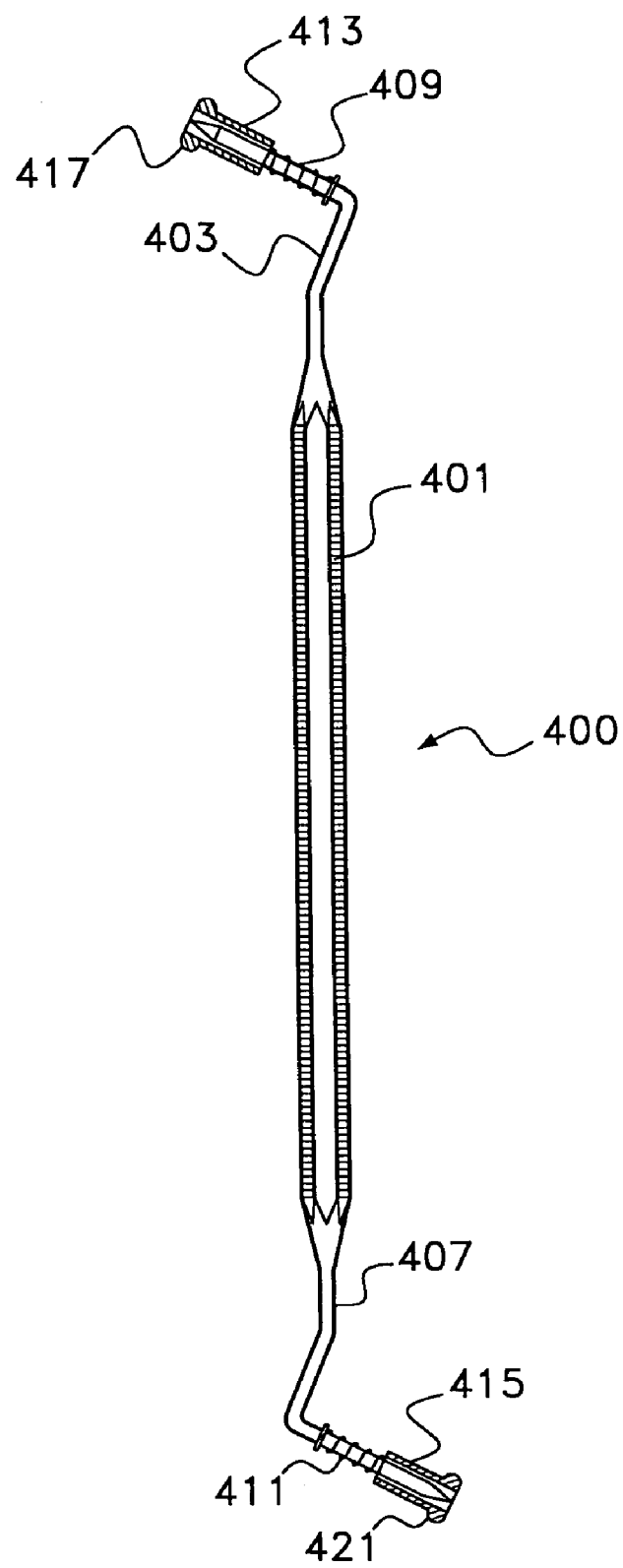

FIG. 12 shows a front view of a preferred alternative embodiment present invention device 400 that functions similarly to device 201 described above, except with opposing, different size bases/footprints at opposite ends for choice of use. Device 400 has a handle member 401 with opposing ends both being operative ends. Thus, end 403 has a spring 409 and a base/footprint 417 of a larger diameter, with base 413 having a hollow center that conceals the pointed end in the rest position, and is connected to the spring 409 for punch-pierce movement, such as is described above. Likewise, end 407 has a spring 411 and a different size footprint 421 of a smaller diameter, with base 415 having a hollow center that conceals the pointed end in the rest position, and is connected to the spring 411 for punch-pierce movement, as described above.

Obviously, numerous modifications and variations of the present invention are possible in light of the above teachings. It is therefore understood that within the scope of the appended claims, the invention may be practiced otherwise than as specifically described herein.

What is claimed is:

1. An implant placement locator instrument, which comprises:
   an elongated handle member, said handle member having a first end and a second end, each of said first end and said second end being an operative end, each said operative end including:
   a base having a footprint of an implant post, said base having a hollow center, said hollow center adopted to hold a punch;
   a punch located on said instrument at said operative end and inside said hollow center of said base, said punch having a pointed tip for piercing bone, said punch having a first position relative to said base, being a retracted position wherein it is retracted within said hollow center, and having a second position relative to said base, being an extended, piercing position wherein it is at least partially extended out of said hollow center;
   a spring connected to one of the said operative end base and said punch so as to enhance movement of said punch from its one of its first position and second position to the other of its first position and second position;
   wherein a user may position said device at a location desirable for an implant post over a bone area and then actuate said instrument to move said punch from its first position to its second position to mark and pierce a bone area for subsequent preparative work for implanting a post, so as to create both a locator mark and a starter piercing for said subsequent preparative work.

2. The instrument of claim 1 wherein said punch is fixedly connected to said operative end of said elongated handle, and said base is moveably connected to said operative end of said elongated handle.

3. The instrument of claim 2 wherein said base is connected to said operative end of said elongated handle via said spring, and said spring biases said base downwardly to a rest position wherein said punch is in its first position.

4. The instrument of claim 1 wherein said base is a hollow cylindrical base.

5. The instrument of claim 2 wherein said base is a hollow cylindrical base.

6. The instrument of claim 1 wherein said elongated handle is a hollow handle and said operative end has a terminus that is said base, and wherein said instrument further includes a punch shaft located within said elongated handle which has an actuation end and a punch end, and said punch end has a terminus that is said punch.

7. The instrument of claim 6 wherein said punch shaft is connected to said elongated handle via said spring, and said spring biases said punch shaft upwardly to a rest position wherein said punch is in its first position.

8. The instrument of claim 7 wherein said first end of said elongated handle has a different size base such that two different sizes are available to a user in a single instrument.

9. The instrument of claim 7 wherein said first end of said elongated handle has a different size base such that two different sizes are available to a user in a single instrument.

10. The instrument of claim 7 wherein said elongated handle includes at least one bend and said punch shaft actuation end extends out of said elongated handle at said bend.

* * * * *